(12) United States Patent
Banerjee (10) Patent No.: US 11,995,970 B2
(45) Date of Patent: May 28, 2024

(54) APPARATUS AND A METHOD FOR GENERATING AN ALERT ASSOCIATED WITH AN EARTHING SYSTEM

(71) Applicant: Sonjib Banerjee, Srinagar (IN)

(72) Inventor: Sonjib Banerjee, Srinagar (IN)

( * ) Notice: Subject to any disclaimer, the term of this patent is extended or adjusted under 35 U.S.C. 154(b) by 103 days.

(21) Appl. No.: 17/419,804

(22) PCT Filed: Sep. 20, 2019

(86) PCT No.: PCT/IN2019/050691
§ 371 (c)(1),
(2) Date: Jun. 30, 2021

(87) PCT Pub. No.: WO2020/144704
PCT Pub. Date: Jul. 16, 2020

(65) Prior Publication Data
US 2022/0092961 A1    Mar. 24, 2022

(30) Foreign Application Priority Data
Jan. 9, 2019   (IN) .............................. 201941000970

(51) Int. Cl.
*G08B 21/18*  (2006.01)
*G01N 27/04*  (2006.01)
*G01N 33/24*  (2006.01)
*G06F 16/901* (2019.01)

(52) U.S. Cl.
CPC ......... *G08B 21/182* (2013.01); *G01N 27/041* (2013.01); *G01N 33/24* (2013.01); *G06F 16/9017* (2019.01)

(58) Field of Classification Search
CPC .... G08B 21/182; G01N 27/041; G01N 33/24; G06F 16/9017
See application file for complete search history.

(56) References Cited

U.S. PATENT DOCUMENTS

2016/0349305 A1* 12/2016 Pal ..................... G01R 31/52

FOREIGN PATENT DOCUMENTS

KR         101516776 B1     5/2015

* cited by examiner

*Primary Examiner* — Hongmin Fan
(74) *Attorney, Agent, or Firm* — Jose Cherson Weissbrot (57) ABSTRACT

The invention provides an apparatus and a method for generating an alert associated with an earthing system. The method includes receiving, by a processor, a resistivity value of an earthing system captured by one or more sensors during operational and fault time. The method may further include comparing, by a processor, the resistivity value with a predetermined threshold value. The method may further include generating the alert associated with the earthing system, based on the comparison of the resistivity value with the predetermined threshold value.

5 Claims, 5 Drawing Sheets

APPARATUS AND A METHOD FOR GENERATING AN ALERT ASSOCIATED WITH AN EARTHING SYSTEM

PRIORITY CLAIM

This application claims priority from the provisional application numbered 201941000970 filed with Indian Patent Office, Chennai on Jan. 9, 2019 entitled "A Method and Apparatus for Remote Fault-time Earth Resistance Monitoring", the entirety of which is expressly incorporated herein by reference.

DESCRIPTION OF THE INVENTION

Technical Field of the Invention

The present invention relates to a measuring apparatus and a method for generating an alert associated with an earthing system during normal operation and fault time. More specifically, the invention relates to an apparatus and method for providing a solution that is aimed to monitor the health of earthing system by performing the task of reading the values of earth pit resistance remotely and executing preemptive management decisions, by integrating the sensors, sensing peripheral units and the supervisory command centers which have the ability to collect, compile and analyze data during normal operation and at the time of fault.

Background of the Invention

Presently, earth pit or earth grids are passive systems whose efficiency depends on continuously varying resistivity of the soil in immediate vicinity of earth conductor. The method of measuring earth pit resistance is a manual process, as mentioned in IEEE 81 2013, BSEN 7430 and other relevant standards, is considered to be more conventional and has its drawback. [0004] The traditional task delegation of operating and measuring the earth pit resistance in a manual process, is often plagued because of the time constraints by the manual process and the task quality is perceived differently by different supervisors. This causes inconsistency in efficiency of manual measurement and often the very best resource gets grossly unrecognized, leading to unsatisfied measurement and monitoring of earth pit resistance. The automated sensing and monitoring of the earth pit resistance plays an important role.

Hence, there exists need for an apparatus and a method for generating an alert associated with health of earthing system in an efficient manner.

SUMMARY OF THE INVENTION

The present invention overcomes the drawbacks in the prior art and provides an apparatus and a method for generating an alert associated with health of earthing system.

In accordance with an embodiment, the apparatus may include at least one memory configured to store instructions and at least one processor configured to execute the instruction to: receive a resistance value of an earthing system captured by one or more sensors. The at least one processor may send the resistance value to cloud based database and compiler where the resistance value is converted to resistivity value and compared with a predetermined threshold value. In accordance with an embodiment, the at least one processor may be configured to transmit the resistance value along with pit id to a database the database converts the resistance value to resistivity value and stores the resistivity value along with its pit id.

In accordance with an embodiment, the at least one processor may be configured to activate a GSM based on the comparison of the instantaneous battery voltage of sensing unit with the predetermined threshold value. The alert includes a text message-based alert. Further, one or more of a video alerts, audio alert can be generated through User Interface.

In accordance with an embodiment, method for generating an alert associated with an earthing system. The method may include receiving, by a processor a resistance value of an earthing system captured by one or more sensors. The method may further include comparing, by a compiler of User Interface, the resistivity value with a predetermined threshold value. The method may further include generating the alert associated with the earthing system, based on the comparison of the resistivity value with the predetermined threshold value.

In accordance with an embodiment, the method may further include determining whether the resistivity value exceeds the predetermined threshold value and generating the alert associated with the earthing system, based on the comparison of the resistivity value with the predetermined threshold value.

In accordance with an embodiment, the method may further include transmitting the resistivity value to a database.

In accordance with an embodiment, the alert may include one or more of a video alerts, audio alert, or a text message-based alert.

This invention transforms the manual process to automated process having capacity of providing continuous online monitoring system that enables detection, recording, trend analysis, annunciation and condition-based maintenance for earthing system. Most importantly, it will perform fault time health analysis of earthing system such that necessary corrections are executed to save life and asset during future faults. This invention also relates to dynamic monitoring of fault time earth resistance with the technology that has ability to sense change in parameters at the time of fault.

OBJECT OF THE INVENTION

This object of the present invention is aimed to allow performing the task of monitoring the earth resistivity in remote means by complete automation with the integration of sensors. The use of sensing the earth resistivity by remote means is possible by the integration of hardware and software module to form an entire electronic device which can monitor the normal time and fault time earth resistance.

The apparatus of Remote Fault Time Earth Resistance Monitoring system is an electronic device whose function is to measure the resistivity of an earthing system installed remotely and this measurement is done within defined time interval and during fault-time scenario. The apparatus comprises of Sensor, Sensing unit, Peripheral Command-centers, Supervisory Command-centers and Central Command-centers.

BRIEF DESCRIPTION OF DRAWINGS

The foregoing and other features of embodiments will become more apparent from the following detailed description of embodiments when read in conjunction with the accompanying drawings. In the drawings, like reference numerals refer to like elements.

In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

DETAILED DESCRIPTION OF THE INVENTION

Reference will now be made in detail to the description of the present subject matter, one or more examples of which are shown in figures. Each example is provided to explain the subject matter and not a limitation. Various changes and modifications obvious to one skilled in the art to which the invention pertains are deemed to be within the spirit, scope and contemplation of the invention.

The invention provides an apparatus and a method for generating an alert associated with an earthing system. The method includes at least one processor configured to execute the instruction to: receive a resistance value of an earthing system captured by one or more sensors, send the resistance value to cloud based database and compiler, where the resistance value is converted to resistivity value and compared with a predetermined threshold value.

As used in the application, the term 'circuitry' or 'circuit' refers to all of the following: (a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

Figure 1:
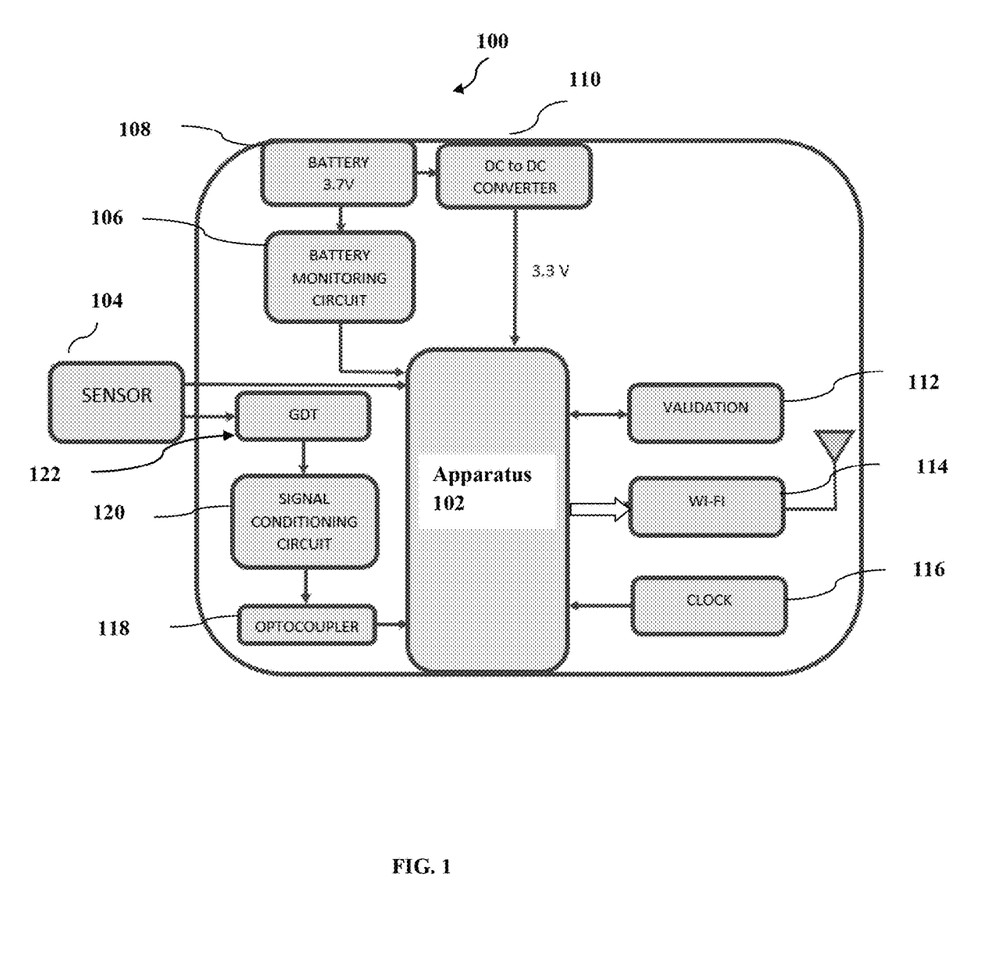
FIG. 1 illustrates a block diagram of an apparatus with one or more sensory components to measure earth pit resistance associated with an earthing system and transmit the same with unidirectional communication, according to one embodiment of the invention.

This definition of 'circuitry' applies to all uses of this term in this application, including in any claims. As a further example, as used in this application, the term"circuitry" would also cover an implementation of merely a processor (or multiple processors) or portion of a processor and its (or their) accompanying software and/or firmware. The term"circuitry" would also cover, for example and if applicable to the particular claim element, a baseband integrated circuit or applications processor integrated circuit for a mobile phone or a similar integrated circuit in server, a cellular network device, or other network device. [0026] FIG. 1 illustrates a block diagram of an apparatus with one or more sensory components to measure earth pit resistance associated with an earthing system and transmit the same with unidirectional communication, according to one embodiment of the invention.

Figure 2:
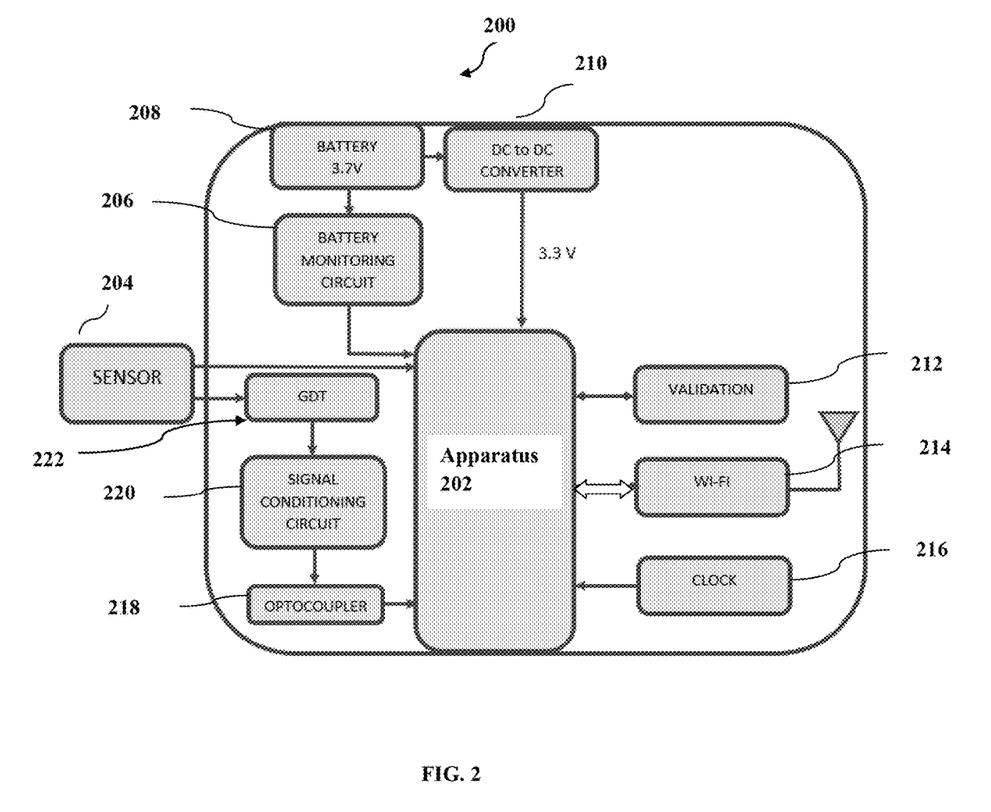
FIG. 2 and FIG. 3 illustrate a block diagram of an apparatus with one or more sensory components to measure earth pit resistance associated with an earthing system and transmit the same with bidirectional communication, according to one embodiment of the invention.

FIG. 2 illustrates a block diagram of an apparatus with one or more sensory components to measure earth pit resistance associated with an earthing system and transmit the same with bidirectional communication, according to one embodiment of the invention.

In an embodiment, the components may include one or more sensors 104/204, a battery mounting circuit 104/204, a battery 108/208, a DC-DC converter 110/210, validation 112/212, network interface as WI-FI 114/214, a clock generator 116/216, optometer 118/218, a signal conditioning circuit 120/220.

In accordance with an embodiment, a plurality of sensors 104/204 may capture the resistance of the earthing system. Sensor is buried in the soil to detect differential stress at sensing ports. In some example embodiments, the sensors 104/204 may house in a corrosion proof metallic structure. In some example embodiments, the sensors 104/204 may configured within the component. In some example embodiments, the EM protection may be achieved through appropriate Faraday cage. The sensors 104/204 may be hardwired to the sensing unit using EM compatible cable.

In some example embodiments, the sensors 104/204 may comprise a power module, an input module, a communication module and a controller. In some example embodiments, the power module has 3.7 V Lithium-ion battery, 3.7 to 3.3 V DC to DC Converter and online battery voltage monitoring circuit. The input module has operation & fault time measurement circuit with necessary surge protection, voltage control and barrier. The communication module has an Xbee wi-fi (2.9 to 3.3 V at 2.4 GHz) with a range of 2.2 km as per datasheet. The controller module has Atmel 8-bit AVR RISC IC (3.3 V, 8 MHz), Crystal oscillator.

In some example embodiments, the sensors 104/204 may include an operational measurement circuit. The Operational measurement circuit (OMC) wakes up the sensor at predefined time interval to measure the differential stress at sensing port. It controls sleep and wake up function is to increase life span of battery.

In some example embodiments, a Fault Alert Circuit (FAC) wakes up the sensor and triggers it to record the earth pit resistance at fault-time. Surge protection, voltage control and barrier circuits are components of FAC. The Sensing Unit is housed in IP68 cabinet with appropriate termination mechanisms.

In some example embodiments, the sensors 104/204 reads the earth pit resistance value at pre-programmed time steps. Time steps can be programmed as per client requirement. In some example embodiments, the sensors 104/204 may be received by AVR Controller for necessary analysis.

Figure 3:
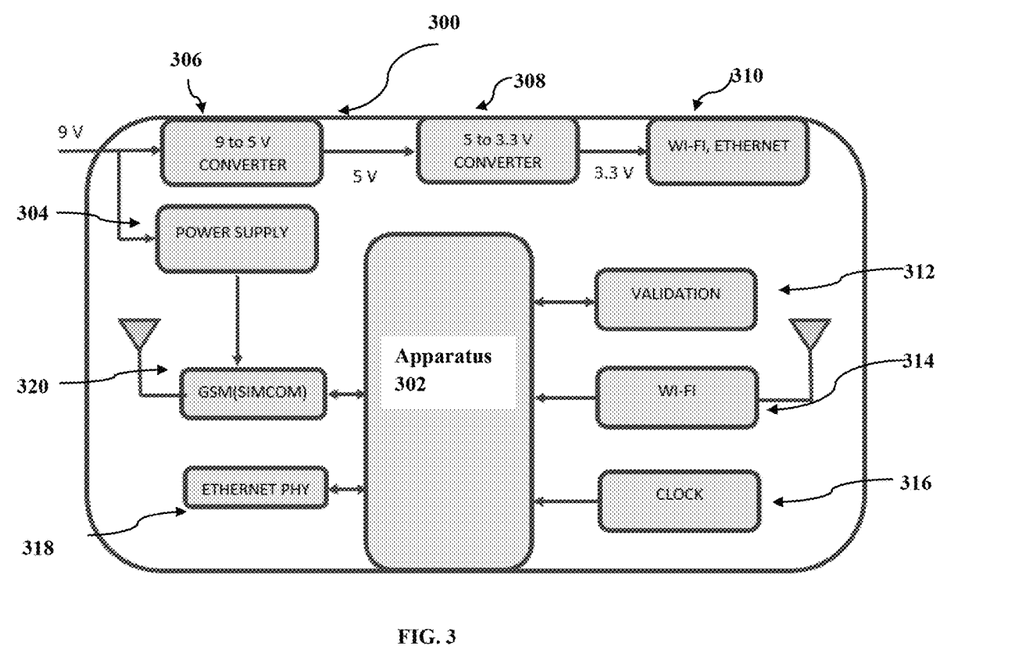

In some example embodiments, the measured resistance value and battery voltage of SSU is sent to Xbee Wireless module 114. Further, SSU Xbee 114 transmits these values to MSU Xbee 214. In some example embodiments, the measured resistance value and battery voltage of MSU is sent to Xbee Wireless module 214. Further, MSU Xbee 214 transmits all values to PCC Xbee 314.

The surge voltage appears across the terminals of GDT 122/222 at the time of fault. The GDT sparks above 60V. Output of GDT is applied to the signal conditioning Circuit 120/220 to step down the voltage to 1.5 V. This signal is applied to optocoupler 118/218.

In some example embodiments, the optocoupler 118/218 activates and triggers the AVR Controller. In turn, AVR Controller triggers the sensor to take pit resistance reading at that instant.

The battery monitoring unit 106/206 checks battery level to alert personnel for maintenance/replacement.

Figure 4:
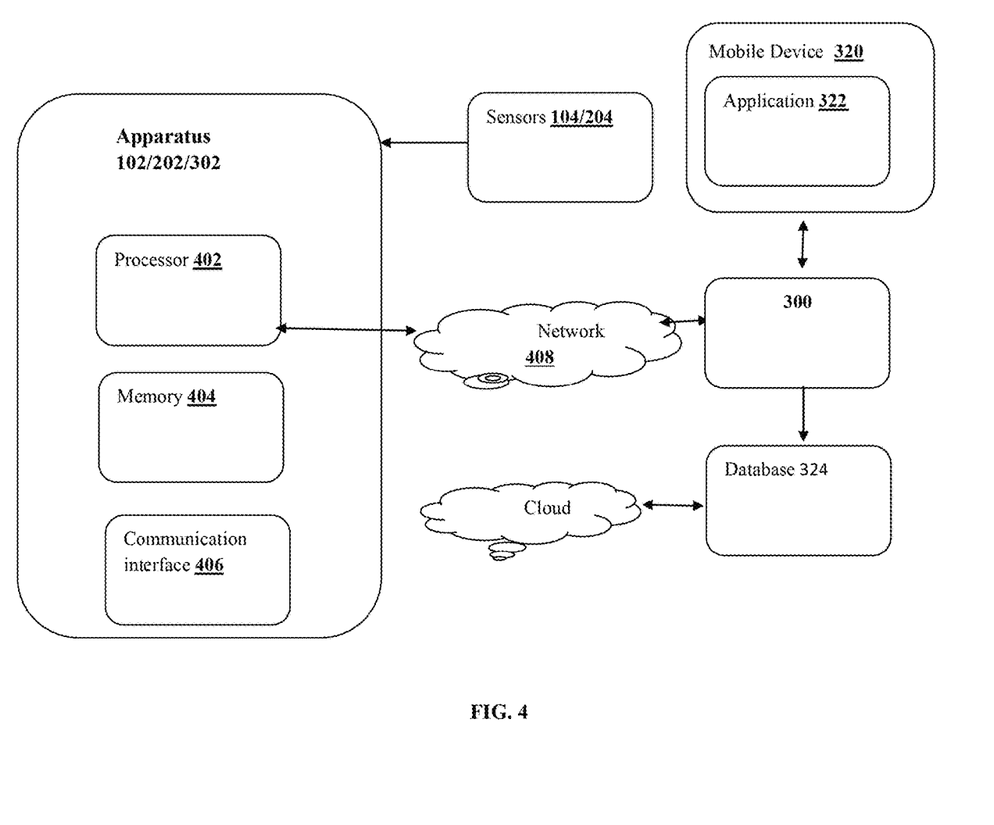
FIG. 4 illustrates a block diagram of an apparatus for transmitting earth pit resistance along with pit id to the database and generating an alert associated with battery conditioning of the sensing unit of earthing system

FIG. 4 illustrates a block diagram of an apparatus for generating an alert associated with an earthing system.

In an alternative embodiment, dedicated hardware implementations, such as application specific integrated circuits, programmable logic arrays and other hardware devices, can be constructed to implement one or more of the methods described herein. Applications that may include the apparatus of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The apparatus may include a processor 402, a memory 404, a communication interface 406, one or more sensors 104/204, a database 324, a network 408 and a mobile device 320 includes an application 322.

In accordance with an embodiment, the processor 202 402 may be of any type of processor, such as 32-bit processors using a flat address space, such as a Hitachi SHI, an Intel 80386, an Intel 960, a Motorola 68020 (or other processors having similar or greater addressing space). Processor types other than these, as well as processors that may be developed in the future, are also suitable. The processor may include general processor, Digital Signal Processing (DSP) chip, an Application Specific Integrated Circuit (ASIC), Field Programmable Gate Arrays (FPGAs), etc.), firmware or a combination thereof.

Processors suitable for the execution of a computer program include, by way of example, both general and special purpose microprocessors, and anyone or more processors of any kind of digital computer. Generally, a processor receives instructions and data from a read only memory or a random-access memory or both. The essential elements of a computer are a processor for performing instructions and one or more memory devices for storing instructions and data. Generally, a computer also includes, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a GPS receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The memory may be a non-transitory medium such as a ROM, RAM, flash memory, etc. The processor and the memory can be supplemented by, or incorporated in, special purpose logic circuitry.

The processes and logic flows described in the specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). [0044] In accordance with an embodiment, the memory 404 includes both dynamic memory (e.g., RAM, magnetic disk, writable optical disk, etc.) and static memory (e.g., ROM, CD-ROM, etc.) for storing executable instructions that when executed perform the inventive steps described herein to generate an alert associated with an earthing system. [0045] In accordance with an embodiment, network 408 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (Wi-Fi), wireless LAN (WLAN), Bluetooth®, Internet Protocol (IP) data casting, satellite, mobile ad-hoc network (MANET), and the like, or any combination thereof.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

In accordance with an embodiment, the processor is 402 configured to execute the instruction to: receive a resistance value of an earthing system captured by one or more sensors.

In some example embodiments, the processor 402 may be configured to send the resistance value to cloud based database and compiler, where the resistance value is converted to resistivity value and compared with a predetermined threshold value. [0049] In accordance with an embodiment, the processor 402 may be configured to generate an alert associated with an earthing system monitor is performed when earth resistivity or battery voltage breaches threshold value.

The resistivity value and battery voltage may be sent to one or more mobile device. The mobile device 320 may be any mobile computer including, but not limited to, vehicle telemetry device or sensor, a personal navigation device ("PND"), a portable navigation device, a cellular telephone, a mobile phone, a personal digital assistant ("PDA"), a wearable device, a computer and/or other device. In some embodiments, it is contemplated that mobile computer can refer to a combination of devices such as a cellular telephone that is interfaced with an on-board navigation system of an autonomous vehicle or physically connected to the vehicle.

In accordance with an embodiment, the processor 402 may be configured to, send the resistance value to cloud based database and compiler, where the resistance value is converted to resistivity value and stores the resistivity value along with its pit id.

In accordance with an embodiment, the processor 402 may be configured to activate a GSM based on the battery voltage value and comparison of the resistivity value with the predetermined threshold value. The activation of GSM leads to an alert to be sent to the one or more mobile devices 320. The alert includes one or more of a video alerts, audio alert, or a text message-based alert.

Figure 5:
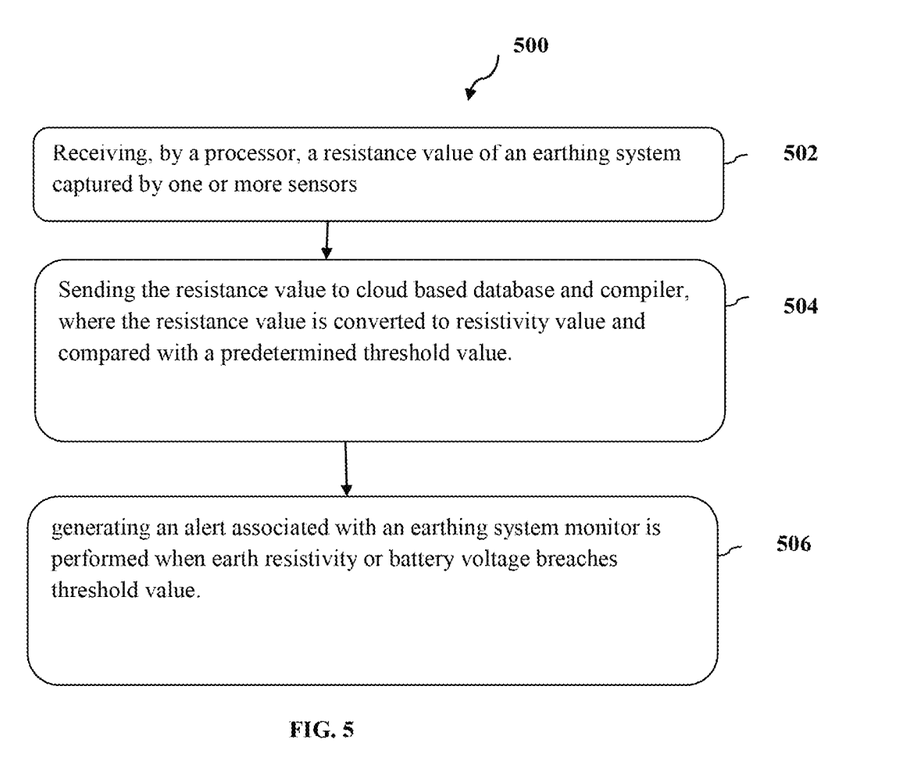
FIG. 5 illustrates a block diagram of a method for receiving of resistance value from one or more sensors associated with an earthing system and transmitting the same wirelessly to apparatus shown in FIG. 4, which in turn transmits earth pit resistance along with pit id to the cloud-based database and compiler. Generating an alert associated with an earthing system monitor is performed when earth resistivity or battery voltage breaches threshold value.

FIG. 5 illustrates a method for generating the alert associated with the earthing system, according to one embodiment of the invention.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionalities as described herein.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

In accordance with an embodiment, method for generating an alert associated with an earthing system may comprise at step 502, receiving, by a processor a resistance value of an earthing system captured by one or more sensors.

In accordance with an embodiment, at step 504, sending resistance value to cloud based database and compiler, where the resistance value is converted to resistivity value and compared with a predetermined threshold value.

In accordance with an embodiment, at step 506, generating an alert associated with an earthing system monitor is performed when earth resistivity or battery voltage breaches threshold value. The method may further include determining whether the resistivity value exceeds the predetermined threshold value and generating the alert associated with the earthing system, based on the comparison of the resistivity value with the predetermined threshold value.

In accordance with an embodiment, the method may further include transmitting the resistivity value to a cloud-based database and compiler. In accordance with an embodiment, the alert may include one or more of a video alerts, audio alert, or a text message-based alert.

Thus, the invention provides condition monitoring of earth pit during normal operation and at the time of fault, automated scheduling of maintenance for earth pit, timely maintenance prevents production loss, malfunctioning of protection system, life and asset.

Further, self-powered sensing units with automatic sleep functions to increase battery life. The apparatus identifies and intimate chronic circuits having earth fault to regulatory/governing authorities. This invention transforms the manual process to automated process having capacity of providing continuous online monitoring system that enables detection, recording, trend analysis, annunciation and condition-based maintenance for earthing system. Most importantly, it will perform fault time health analysis of earthing system such that necessary corrections are executed to save life and asset during future faults. This invention also relates to dynamic monitoring of fault time earth resistance with the technology that has ability to sense change in parameters at the time of fault The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. An apparatus for generating an alert associated with an earthing system, the apparatus comprising:
one or more sensors configured to measure an earth pit resistance value associated with the earthing system;
at least one memory configured to store instructions;
at least one processor configured to execute the instructions to:
receive a resistance value of the earthing system from the one or more sensors;
send the captured earth pit resistance value along with a pit id to a cloud-based compiler and a database, wherein the cloud-based compiler is configured to convert the captured earth pit resistance value to a resistivity value;
compare the resistivity value with a predetermined threshold value;
determine a fault time earth resistance of the earthing system, based on the resistivity value, wherein the fault time earth resistance is an earth pit resistance value at a time of fault;
generate an alert associated with the earthing system when:
an occurrence of an earth fault,
the resistivity value exceeds the predetermined threshold value, or
a battery voltage breaches a threshold value wherein to generate the alert associated with the earthing system, the at least one processor is further configured to activate a GSM, based on occurrence of lightning or earth fault or comparison of the resistivity value with the predetermined threshold value, and the battery voltage with the threshold value; and transmit the battery voltage to the cloud-based compiler and the database.

2. The apparatus as claimed in claim 1, wherein to generate the alert associated with the earthing system having the one or more sensors, the at least one processor is configured to:

determine whether the resistivity value exceeds the predetermined threshold value;

generate the alert associated with the earthing system if the resistivity value exceeds the predetermined threshold value; and transmit the alert to regulatory bodies, disaster management cell, fire department regarding circuits chronically prone to earth fault and locations chronically prone to lightning.

3. The apparatus as claimed in claim 2, wherein in the cloud-based compiler, the captured earth pit resistance value is converted to the resistivity value, and the database stores the resistivity value along with the pit id.

4. The apparatus as claimed in claim 1, wherein the alert includes one or more of video alerts, an audio alert, a mail alert or a text message-based alert.

5. A method for generating an alert associated with an earthing system having one or more sensors, the method comprising the steps of:

receiving, by a processor, an earth pit resistance value associated with an earthing system, wherein the earth pit resistance value is measured by the one or more sensors;

sending the earth pit resistance value to a cloud-based compiler and a database, wherein the earth pit resistance value is converted to a resistivity value and compared with a predetermined threshold value;

determining a fault time earth resistance of the earthing system, based on the resistivity value, wherein the fault time earth resistance is an earth pit resistance value at a time of fault; and generating an alert associated with the earthing system having the one or more sensors when:

an occurrence of an earth fault occurs, the resistivity value exceeds the predetermined threshold value, or a battery voltage breaches a threshold value; and wherein generating the alert associated with the earthing system further comprises the step of transmitting the alert to regulatory bodies, disaster management cell, fire department regarding circuits chronically prone to earth fault and locations chronically prone to lighting; and transmitting the fault time earth resistance value and the battery voltage to the cloud-based compiler and the database.

* * * * *